United States Patent [19]

Burrows et al.

[11] Patent Number: 5,434,880
[45] Date of Patent: Jul. 18, 1995

[54] LASER SYSTEM

[75] Inventors: Graham Burrows, Rugby; David Gurwicz, Gateshead, both of United Kingdom

[73] Assignee: Lumonics Ltd., United Kingdom

[21] Appl. No.: 82,769

[22] Filed: Jun. 28, 1993

[30] Foreign Application Priority Data

Jul. 11, 1992 [GB] United Kingdom ............... 9214796

[51] Int. Cl.⁶ .................. H01S 3/09; H01S 3/00
[52] U.S. Cl. ............................. 372/69; 372/10; 372/38; 372/51; 372/54; 372/70; 372/82; 372/87
[58] Field of Search ..................... 372/10, 20, 21, 22, 372/38, 39, 40, 55, 61, 69, 70, 71, 72, 82, 87, 92, 97, 51, 54; 315/220, 221, 222, 210, 148

[56] References Cited

U.S. PATENT DOCUMENTS

| | | | |
|---|---|---|---|
| 3,477,037 | 11/1969 | Seitz | 372/51 X |
| 3,881,088 | 4/1975 | Karras | 372/69 X |
| 3,988,699 | 10/1976 | Zachariasse | 372/51 X |
| 4,041,414 | 8/1977 | Richardson et al. | 372/87 X |
| 4,291,254 | 9/1981 | Arlt et al. | 315/240 |
| 4,507,789 | 3/1985 | Daly et al. | 372/92 |
| 4,525,650 | 6/1985 | Hicks et al. | 315/226 |
| 4,544,863 | 10/1985 | Hashimoto | 315/209 |
| 4,554,667 | 11/1985 | Kaminski | 372/87 X |
| 4,641,061 | 2/1987 | Munson | 315/210 |
| 4,730,147 | 3/1988 | Kroening | 315/100 |
| 4,748,635 | 5/1988 | McLellan | 372/87 |
| 4,877,997 | 10/1989 | Fein | 313/634 |
| 4,956,583 | 9/1990 | Lawrence et al. | 315/220 |
| 5,097,472 | 3/1992 | Chenausky | 372/38 |
| 5,109,387 | 4/1992 | Garden et al. | 372/54 X |
| 5,255,277 | 10/1993 | Carvalho | 372/69 X |
| 5,258,994 | 11/1993 | Haruta et al. | 372/69 X |
| 5,291,510 | 3/1994 | Gidon et al. | 372/69 |

FOREIGN PATENT DOCUMENTS

| | | | |
|---|---|---|---|
| 0121917A1 | 4/1984 | European Pat. Off. | 315/220 X |
| 0236670A1 | 9/1987 | European Pat. Off. | 372/69 X |
| 0240049A1 | 10/1987 | European Pat. Off. | 315/220 X |
| 0449168A2 | 10/1991 | European Pat. Off. | 315/220 X |
| WO91/20172 | 12/1991 | European Pat. Off. | 372/69 X |
| 0460247A1 | 12/1991 | European Pat. Off. | 372/69 X |
| 3830361 | 3/1990 | Germany | 372/69 X |
| 1-201975A | 8/1989 | Japan | 372/69 X |
| 1-206678 | 8/1989 | Japan | 372/69 X |
| 1281500 | 7/1972 | United Kingdom | 372/38 X |

OTHER PUBLICATIONS

Koechner, "Solid-State Laser Engineering" 1988 no month Springer Series in Optical Sciences pp. 291-309.
"Solid State Laser Engineering", Walter, Koechner, Springer Verlage 1988, pp. 247 to 292.
Applied Optics, vol. 22, No. 9, May 1983, New York, pp. 1325-1328, Richards et al., "Operation on Krypton-Filled Flashlamps at High Repetition Rates".
Patent Abstracts of Japan, vol. 14, No. 429 (E-978)(4372) 14 Sep. 1990 and JP-A-02 165 683 (Hitachi) 26 Jun 1990.

Primary Examiner—Brian Healy
Attorney, Agent, or Firm—Nixon & Vanderhye

[57] ABSTRACT

A laser system comprises an optical head, a power supply and a computer for controlling the power supply. The optical head comprises a pair of mirrors and four pumping sections. Each pumping section comprises a pair of gas discharge lamps pumping an Nd:YAG laser element. The power supply provides the lamps with alternating current at 25 kHz so that the laser system produces a continuous, modulated or pulsed output light beam. The power supply comprises three boost converters connected in parallel for converting three phase mains supply to direct current and four DC-AC converters. Each DC-AC converter converts the DC output from the boost converters to an AC supply for the lamps of a respective one of the pumping sections. Each DC-AC converter comprises a resonant circuit having an inductor and capacitor connected in series, the lamps being connected across the capacitor, a pair of transistors for conducting current through the resonant circuit in alternating directions, and a control circuit for the transistors. The power supply is also arranged to supply alternating current at a relatively high voltage to the lamps for triggering a discharge. In a modification, the output of the power supply is rectified before it is supplied to the lamps.

28 Claims, 11 Drawing Sheets

LASER SYSTEM

BACKGROUND OF THE INVENTION

This invention relates to a laser system which can operate in a continuous, modulated or pulsed mode and which comprises a pumping section and a power supply for supplying power to the pumping section, the pumping section comprising a solid or liquid laser medium and at least one lamp for providing pumping energy to the laser medium. This invention also relates to a lamp system.

In a conventional laser system, the power supply supplies continuous or pulsed direct current to the lamp. In view of the negative impedance characteristics of the lamp, the power supply includes inductors and capacitors to control and restrict the current flowing through the lamp. Consequently, the power supply is large and costly.

SUMMARY OF THE INVENTION

It is one object of this invention to provide a laser system in which the above mentioned disadvantages are overcome or reduced.

According to one aspect of this invention, there is provided a laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed inside a lamp envelope, and the power supply means being arranged to supply current having a repetitive waveform at a frequency greater than 5 kHz to said at least one lamp.

Although the power supply will still require inductors and capacitors, these are all relatively small as they are operating at a relatively high frequency. Thus, in this laser system, the cost and size of the power supply are much smaller than those of a power supply in a conventional laser system. The time constant of the lamp become progressively more significant at frequencies in excess of 5 kHz and so smoothes the ripple in the output power of the laser system. Where the laser beam is used for a material processing operation on a workpiece, the thermal capacity of the workpiece provides further smoothing.

In order to start a discharge in a lamp, it must be triggered with a relatively high voltage. After the discharge has started, it may be sustained with a relatively low voltage. When a lamp is provided with direct current for triggering it, the need to provide a high triggering voltage causes difficulties in the design of both the power supply and the pumping section. These difficulties increase with the power of the lamp.

Accordingly, it is another object of this invention to provide a new or improved laser system in which these difficulties are reduced.

According to a second aspect of this invention, there is provided a laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed inside a lamp envelope, and the power supply means comprising means for triggering a discharge in said at least one lamp and means for sustaining a discharge in said at least one lamp, the triggering means being arranged to supply alternating current to said at least one lamp at a relatively high voltage, and the sustaining means being arranged to supply current to said at least one lamp at a relatively low voltage.

When the lamp is triggered with alternating current, the voltage required to trigger a discharge is much lower than the voltage which is required when using direct current. Consequently, the design of both the power supply and the pumping section is simplified.

In view of the highly non-linear impedance characteristics of a lamp containing material for supporting a discharge, it is advantageous to provide a power supply for such a lamp which functions as a current source rather than as a voltage source and which supplies current to the lamp at a value which is not dependent upon the impedance of the lamp.

It is a further object of this invention to provide a laser system having a power supply which has the advantage set out above.

According to a third aspect of this invention, there is provided a laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed in a lamp envelope, and the power supply means comprising at least one boost converter for providing a source of direct current, a resonant circuit having a pair of reactive elements in the form of an inductor and a capacitor connected in series, said at least one lamp being connected across one of the reactive elements, a first switching device arranged to conduct current in one direction from the direct current source through the resonant circuit, a second switching device arranged to conduct current in the other direction from the direct current source through the resonant circuit, and means for driving the switching devices to conduct alternately, and thereby cause an alternating current to flow in the resonant circuit.

It is a property of a boost converter that it may act as a current source rather than as a voltage source. Also, by connecting said at least one lamp across the inductor or the capacitor of the resonant circuit as described above, the current through said at least one lamp will not depend upon the impedance of it.

According to a fourth aspect of this invention, there is provided a laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed inside a lamp envelope, and the power supply means being arranged to supply alternating current to said at least one lamp.

BRIEF DESCRIPTION OF THE DRAWINGS

This invention will now be described in more detail, by way of example, with reference to the drawings in which.

DETAILED DESCRIPTION OF THE PREFERRED EMBODIMENTS

Figure 1:
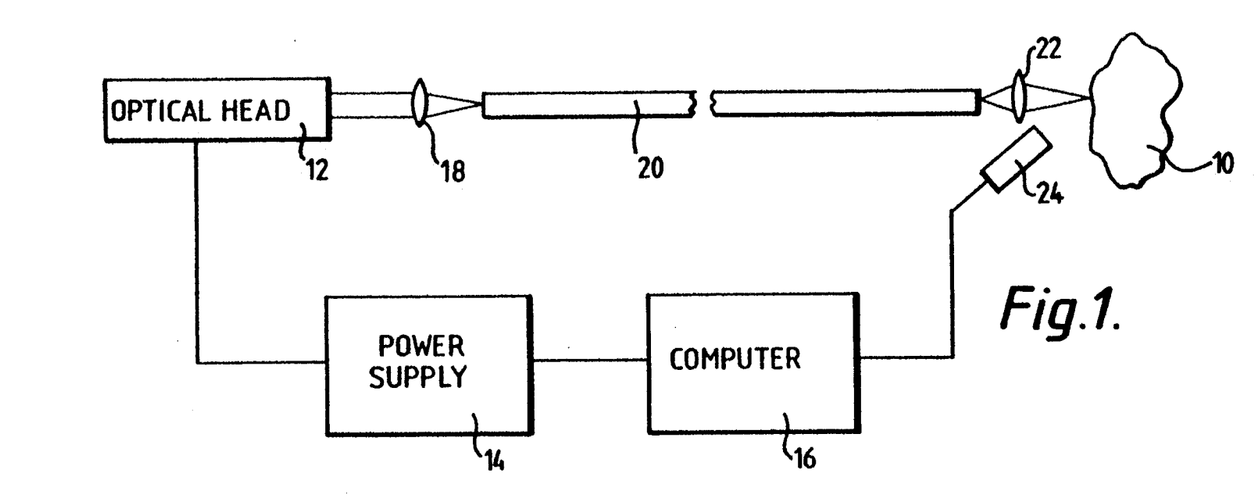
FIG. 1 is a block diagram of a laser system embodying this invention performing a material processing operation on a workpiece.

Referring now to FIG. 1, there is shown a laser system embodying this invention and which is being used to perform a material processing operation on a workpiece 10.

The laser system comprises an optical head 12 which receives power from a power supply 14. The power supply 14 is controlled by a computer 16. The output beam from the optical head 12 is focused by a lens 18 onto the input end of an optical fibre 20. The output beam from the optical fibre 20 is focused by a lens 22 onto the workpiece 10. The material processing operation is monitored by a sensor 24, the output of which is supplied to the computer 16. The computer 16 controls the output beam from the optical head 12 so as to perform the desired processing operation and uses the signal from the sensor 24 to achieve this.

The laser system shown in FIG. 1 is capable of producing an output beam having an average power of 2 kW. However, the present invention is not limited to use in a laser of this power and may be used in both low and high power laser systems excited by one or more lamps. A lower power laser system may have an output power of only a few watts. Laser systems embodying this invention are suitable for performing a wide range of material processing operations on a wide variety of workpieces as well as for other uses. The workpieces may be solid, liquid or gaseous and may also be human or animal tissue. The material processing operations include welding, brazing, cutting, drilling, marking, heat treatment, material curing, and also therapeutic and diagnostic processes performed on human or animal tissue. Other uses include light sources in light shows, holography, pumping other lasers such as dye lasers, and various research applications.

The computer 16 may take the form of the computer used in the JK 704 laser, which is manufactured and supplied by Lumonics Ltd, of Cosford Lane, Swift Valley, Rugby, England. As the design of a computer for use in a laser system is well understood by those skilled in the art, the computer 16 will not be described in further detail.

The computer 16 controls the power supply 14 to the optical head so as to produce either a continuous, modulated or a pulsed output beam. In the case of a continuous output beam, its average power may be set by the user of the computer system. In the case of a pulsed output beam, the duration, shape and energy of each pulse as well as the pulse repetition rate may be set by the user.

Figure 2:
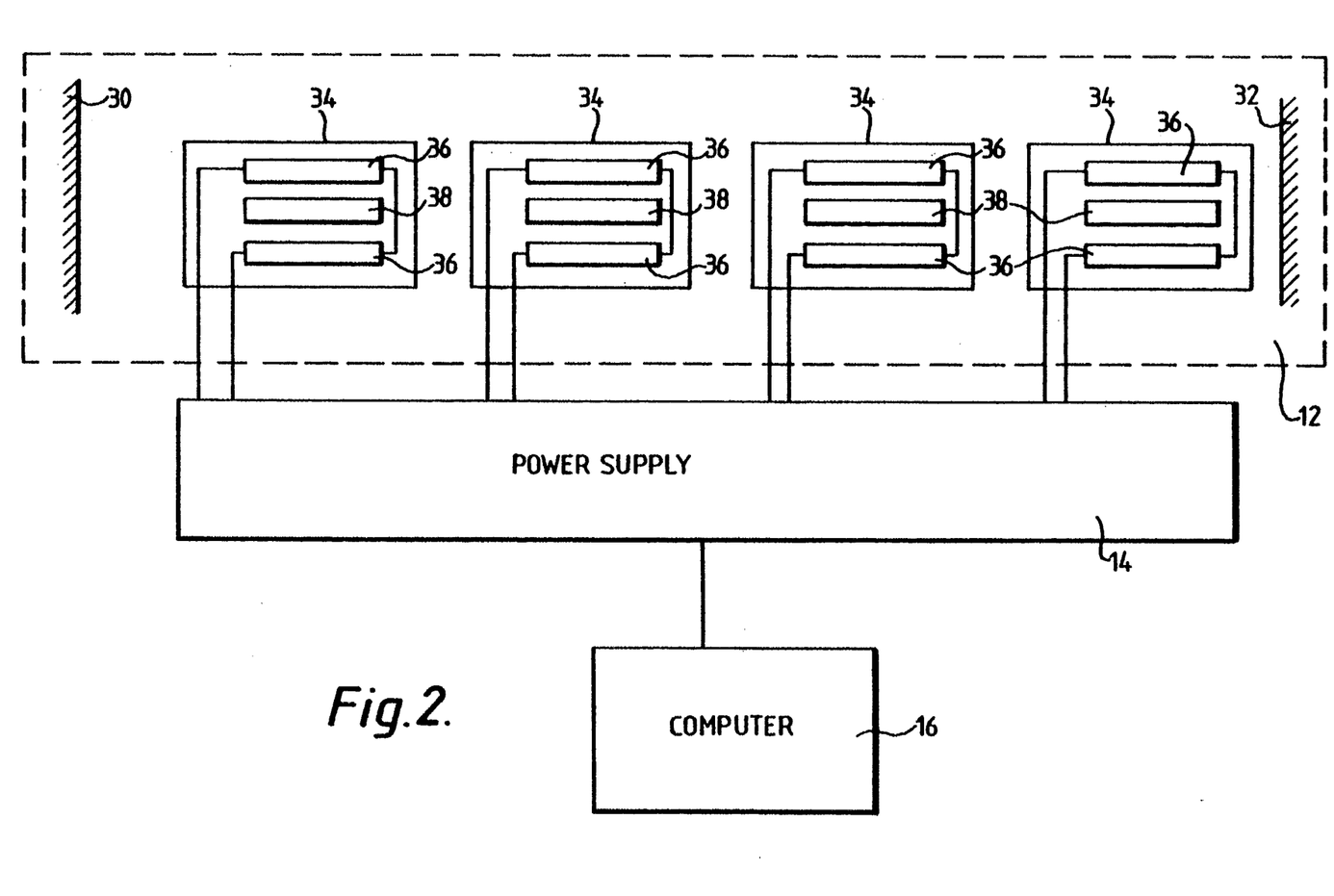
FIG. 2 is a block diagram of the optical head, power supply and computer of the laser system of FIG. 1.

Referring now to FIG. 2, there is shown a block diagram of the optical head 12 and power supply 14 together with their relationship to the computer 16. The optical head 12 has a pair of mirrors 30,32 which together define an optical resonator. Inside this optical resonator, there are four identical pumping sections or chambers 34.

Figure 3:
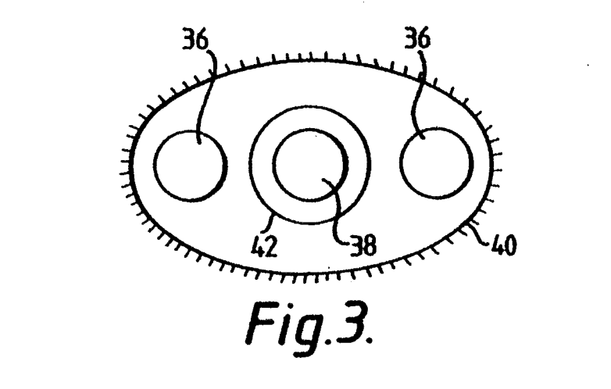
FIG. 3 is a cross-sectional view of a pumping section of the laser system of FIG. 1.

Each pumping section 34 comprises a pair of 8 kW discharge lamps 36 which provide pumping light to a laser element 38. As shown in FIG. 3, in each pumping chamber 34 the two lamps 36 and the laser element 38 are surrounded by a reflector 40. Also as shown in FIG. 3, the laser element 38 is surrounded by a water jacket 42. In operation, filtered, deionised cooling water passes through the water jacket.

The laser element 38 is a solid rod of active laser medium in the form of YAG doped with 0.9% neodymium oxide by weight. As is well known, Nd:YAG emits light at a wavelength of 1064 nm. Nd:YAG represents only one example of active laser media which may be used with the present invention. Moreover, a rod is only one of the possible configurations of the laser medium. A wavelength of 1064 nm is outside the visible spectrum and the present invention may be used with an active laser medium which emits light either inside or outside the visible spectrum.

The present invention may also be used in a laser in which the laser medium is a liquid, for example, rhodamine 6G in ethanol or $Nd^{3+}$ in selenium oxychloride ($SeOCl_2$).

Figure 4:
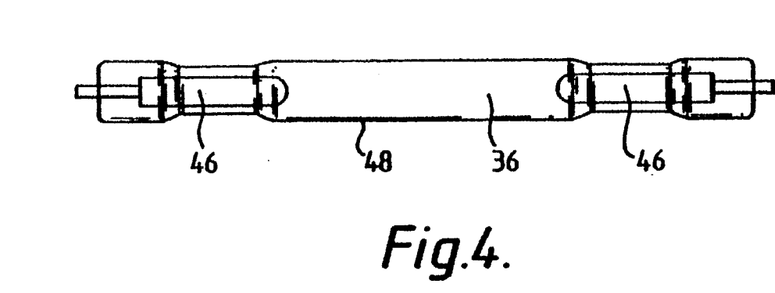
FIG. 4 is an elevational view of a lamp forming part of a pumping section of the laser system of FIG. 1.

As shown in FIG. 4, each lamp 36 comprises a pair of identical electrodes 46 sealed inside a quartz envelope or tube 48. In order to support a discharge between the electrodes 46, the quartz tube 48 contains krypton gas at a pressure of 800 torr. As will be described in greater detail below, the lamps 36 are energised with alternating current at a frequency of 25 kHz. Although the pressure of 800 torr is not critical, the gas pressure should be selected so as to avoid acoustic resonances. The present invention may be used with discharge lamps using materials other than krypton for supporting the discharge. Also, appropriate additional electrodes may be provided in each lamp, for example to assist starting the discharge.

The mirrors 30,32 are plane parallel mirrors formed from coated quartz. On its side facing towards the middle of the optical resonator, the mirror 30 has a reflectivity in excess of 99%. The mirror 32 is the output mirror of the optical head 12 and, on its side facing the middle of the optical resonator, it has a reflectivity of 40%.

In each pumping chamber 34, one electrode 46 of one lamp is connected to one electrode 46 of the other lamp 36 so that the lamps 36 are connected in series. The power supply 14 is connected to the other electrode 46 of each lamp 36. Thus, the power supply 14 supplies current to the two electrodes 46 of each lamp 36.

As indicated above, the power supply 14 supplies alternating current at a frequency of 25 kHz to the lamps. At a frequency of 25 kHz, each of the lamps 36 has a positive dynamic impedance. As the operating frequency of the power supply is increased, the inductors, capacitors and transformers used in it are reduced in size. This fact makes it possible to design the power supply 14 with inductors, capacitors and transformers which are very much smaller than those used in a power supply of the same power capability and which provides direct current to lamps. This reduction in the size of the inductors, capacitors and transformers also makes a large reduction in the cost of the power supply.

Upon cessation of the supply of discharge current to each of the lamps 36, the emitted light decays with a time period of the order of 40 $\mu$S. As a result, the ripple in the output power from the optical head 12 due to the AC excitation is not significant. Also, many workpieces have a sufficiently large thermal capacity to tolerate some degree of ripple in the laser beam during processing.

The present invention may be used with power supplies operating both below and above 25 kHz. However, as the frequency is reduced, the size of the inductors, capacitors and transformers is increased and the ripple in the output power becomes progressively more significant. The present invention should preferably not be applied to a power supply operating at a frequency below 5 kHz. At frequencies between 5 kHz and 20 kHz, the sound generated by the power supply is audible and may cause disturbance to the operator of the laser system. It is therefore preferred to use a frequency which is equal to, or greater than, 20 kHz The power supply includes semi-conductor switching devices. At the present state of development of such devices, losses become significant at frequencies in excess of 30 kHz. With continuing improvements in switching devices, operation upto 100 kHz should be possible in the future.

Figure 5:
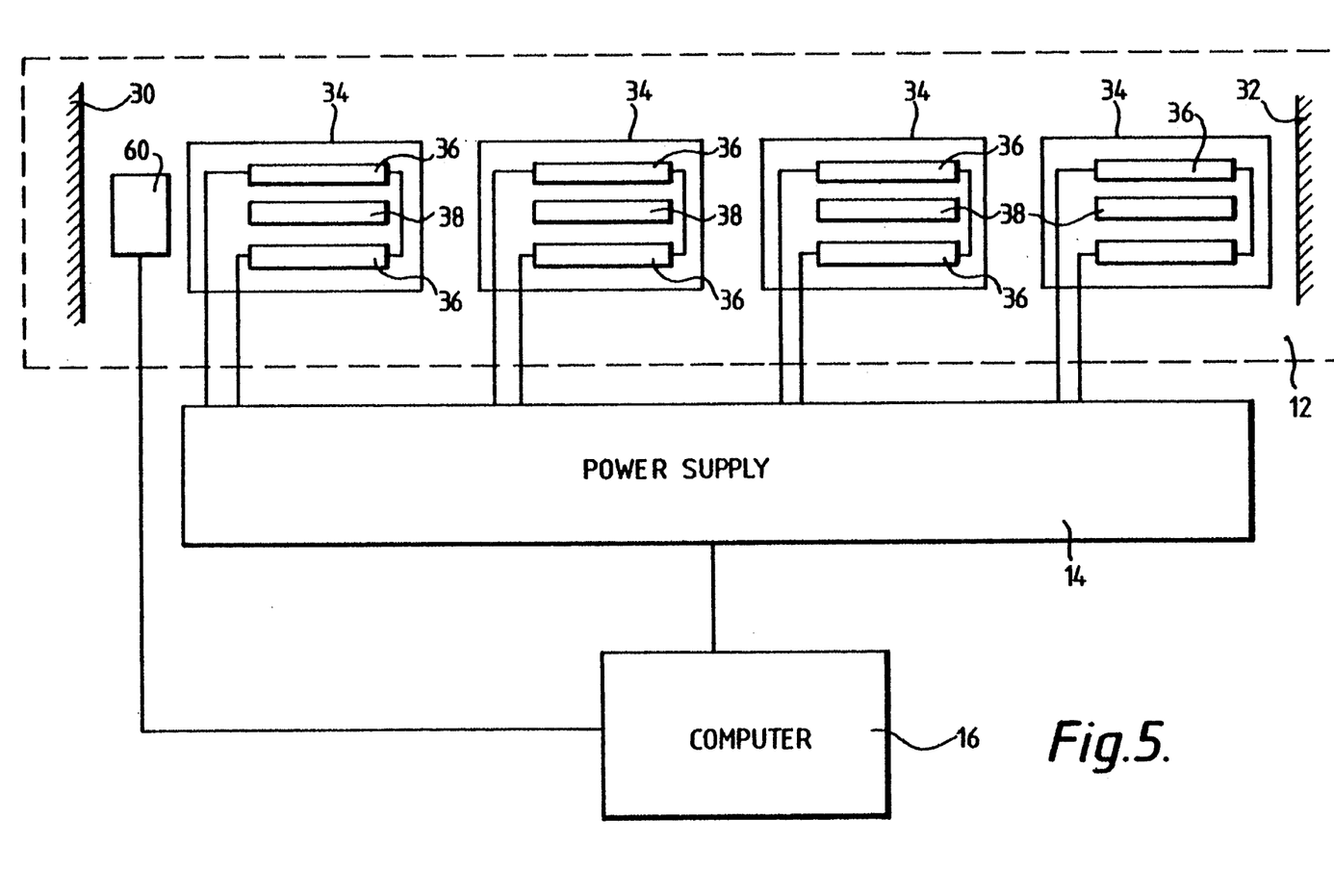
FIG. 5 is a block diagram of the optical head, power supply and computer of the laser system of FIG. 1 provided with a Q-switch.

Referring now to FIG. 5, there is shown a block diagram of the optical head 12, power supply 14 and computer 16 in which the optical head 12 is modified by the inclusion of an acousto-optic modulator 60 which is operated by computer 16. As is well known, the provision of an acousto-optical modulator enables the optical head 12 to be operated in a Q-switched mode.

Figure 6:
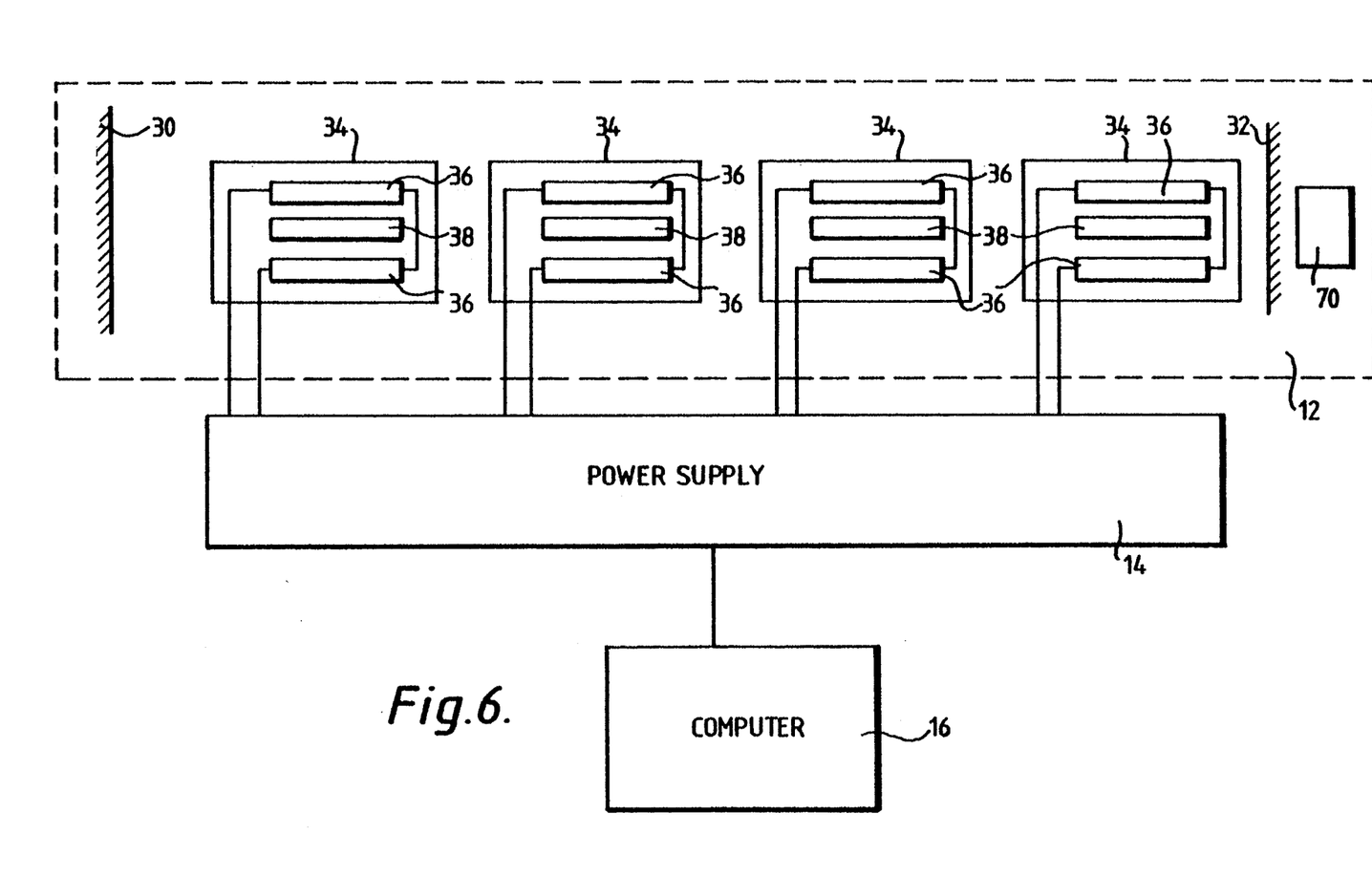
FIG. 6 is a block diagram of the optical head, power supply and computer of the laser system of FIG. 1 modified to include a harmonic generator.

Referring now to FIG. 6, there is shown another block diagram of the optical head 12, power supply 14 and computer 16, in which the optical head 12 is modified by the provision of an harmonic generator 70 positioned in the output beam outside mirror 32. The harmonic generator 70 is a non-linear crystal, for example of deuterated potassium dihydrogen phosphate (DKDP). This crystal has the effect of halving the wavelength of a proportion of the output beam as it passes through it. If desired, two or more crystals may be used in the series. Moreover, as an alternative configuration, harmonic generator 70 may be provided inside the optical resonator.

Although in FIGS. 2, 5 and 6 the present invention is shown in relation to an optical head which has four pumping sections in an optical resonator, the present invention is not limited to this configuration of optical head. The use of four pumping chambers 34 is a convenient way of obtaining a laser beam having a high output power but this number of pumping sections is not critical. The number of pumping chambers may be chosen in accordance with the power and other requirements of the laser and there may be, for example, just a single pumping chamber. The present invention may also be used in an optical head which is configured as an amplifier rather than as an optical resonator. Where the optical head is configured as an amplifier, the mirrors are omitted and light emission from the laser medium is stimulated by an externally generated optical beam. Thus, a set of pumping sections may be organised as a multisection oscillator or an oscillator-amplifier system or a chain of amplifiers.

In comparison with direct current, the use of alternating current for energising the lamps 36 provides two further advantages. Firstly, it leads to an increase in the luminous efficiency of the lamps 36. Secondly, as the electrodes of each lamp wear at the same rate, it leads to an increase in lamp life.

Figure 7:
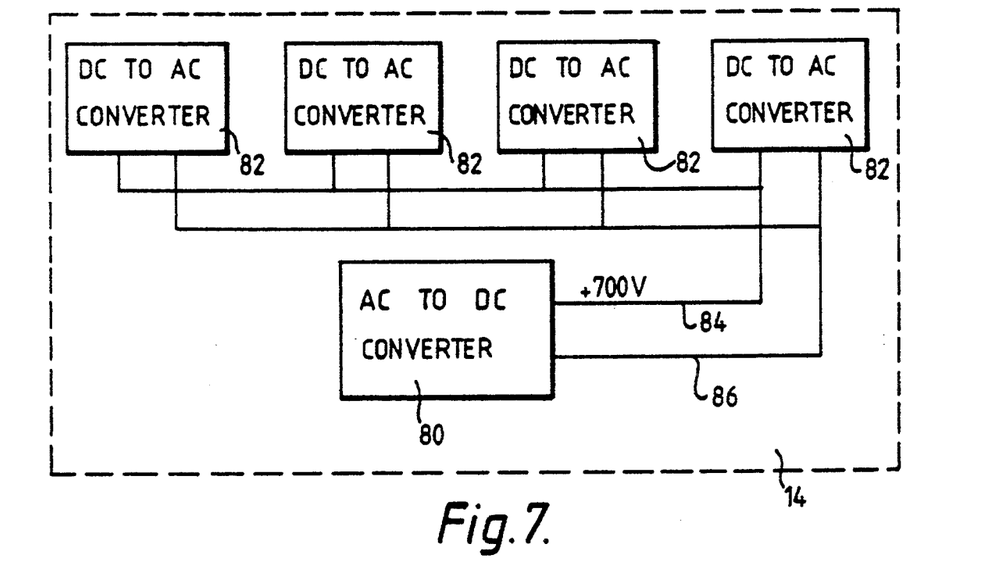
FIG. 7 is a block diagram of the power supply of the laser system of FIG. 1.

Referring now to FIG. 7, there is shown a block diagram of the power supply 14. The power supply 14 comprises an AC to DC converter 80 and four DC to AC converters 82. The converter 80 converts three phase mains frequency to direct current and supplies this at a voltage of 700 V on lines 84,86 to the inputs of the four DC-AC converters 82. Each converter 82 provides the alternating current for energising the lamps 36 of an associated pumping chamber 34. Thus, each pumping chamber 34 has its own DC-AC converter 82.

Figure 8:
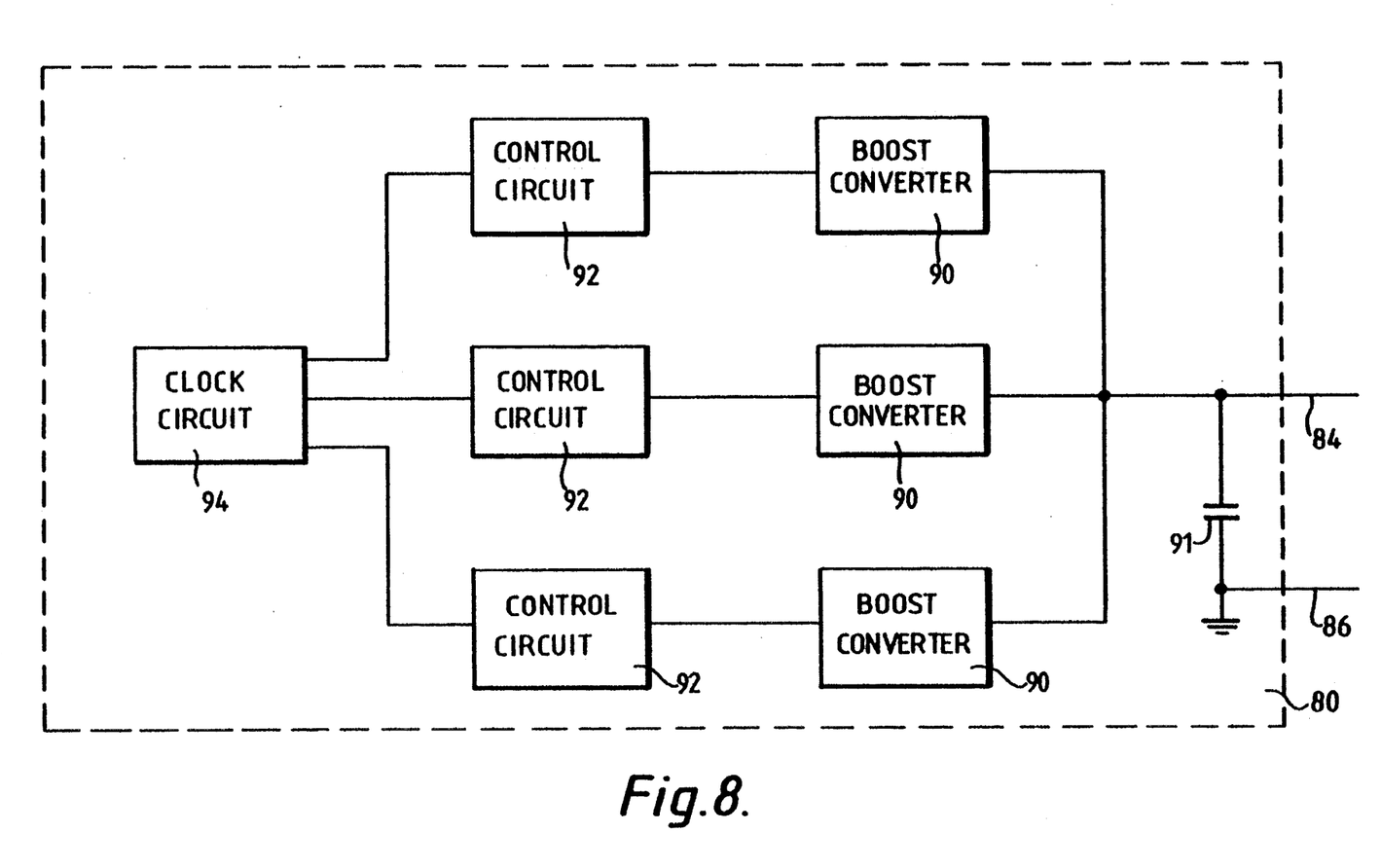
FIG. 8 is a block diagram of the AC to DC converter forming part of the power supply of FIG. 7.

Referring now to FIG. 8, the AC to DC converter 80 comprises three boost converters 90 which supply output current to a capacitor 91. In FIG. 8, the connections between the mains supply and the boost converters 90 are not shown. Each boost converter 90 is controlled by an individual control circuit 92 and each control circuit 92 receives a clock signal from a clock 94. Each of the boost converters 90 operates at a frequency of 25 kHz and the control circuits 92 together with the clock 94 cause the three boost converters 90 to operate at 120° phase intervals. The frequency of 25 kHz is not critical and the frequency of the boost converters 90 does not have to be identical to that of the alternating current supplied to the lamps 36.

Figure 9:
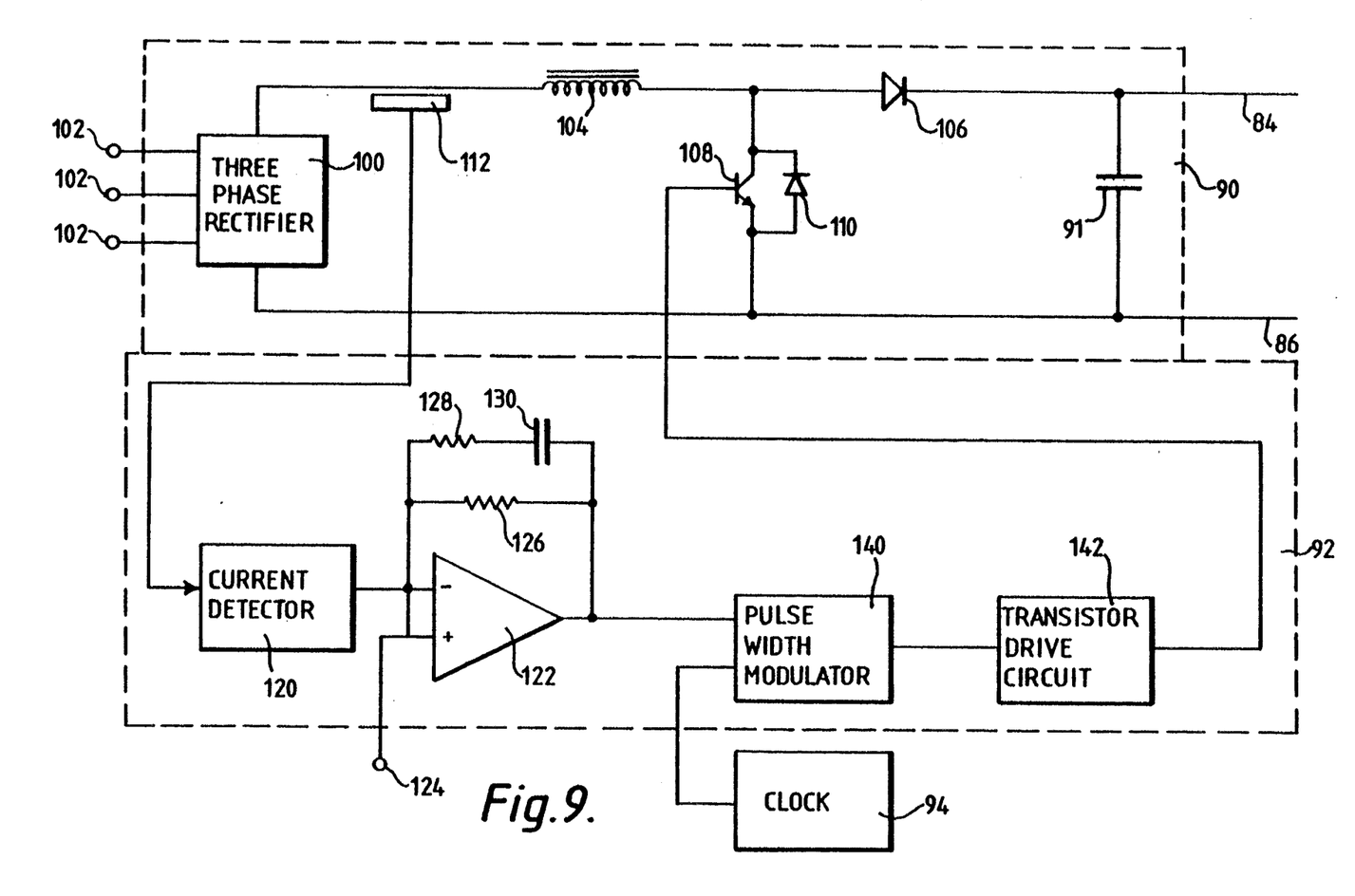
FIG. 9 is a circuit diagram of one of the boost converters and its associated control circuit of the AC to DC converter of FIG. 8.

Referring now to FIG. 9, there is shown the circuit diagram of one of the boost converters 90 together with its associated control circuit 92 and the clock 94. The boost converter 90 comprises a three phase rectifier 100 which receives current from a three phase mains supply on input terminals 102. The positive output of the rectifier 100 is connected through an inductor 104 and a diode 106 to the positive output supply line 84. The negative output of rectifier 100 is connected to the negative output supply line 86. The junction of inductor 104 and the diode 106 is connected to the negative supply line through a transistor 108, whose collector and emitter are bridged by a diode 110. The current flowing through inductor 104 is sensed by a Hall effect current sensor 112.

In the control circuit 92, the output signal from the current sensor 112 is supplied to a current detector circuit 120. The output signal of current detector circuit 120 indicates the level of the current flowing through inductor 104. The output of current detector 120 is connected to the inverting input of a differential amplifier 122. The non-inverting input of differential amplifier 122 receives a current demand signal from computer 16 via a terminal 124. The output and inverting input of amplifier 122 are connected by a circuit comprising resistors 126,128 and a capacitor 130. Thus, amplifier 122 is configured as an integrator. The output from amplifier 122 is connected to one input of a pulse width modulator 140. The other input of pulse width modulator 140 receives a signal from the clock 94. The output of pulse width modulator 140 is connected to the input of a transistor drive circuit 142, which includes an optical link to provide electrical isolation between its input and output. The output of transistor drive circuit 142 is connected to the base of transistor 108.

In operation, the transistor drive circuit 142 supplies a square wave drive signal to transistor 108 at a frequency and phase established by clock 94. The pulse width modulation of this square wave signal is adjusted so as to achieve the current demanded by computer 16. Thus, the boost converter 90 operates as a current source and its output current may be matched to the current requirement of the two lamps 36 which are energised by it. As is well known, the output voltage of a boost converter is greater than its input voltage.

Figure 10:
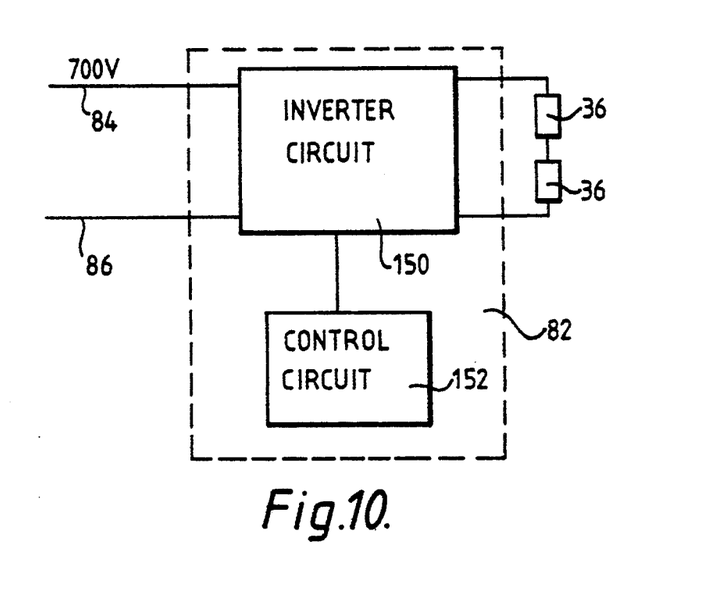
FIG. 10 is a block diagram of one of the DC to AC converters shown in FIG. 7.

Referring now to FIG. 10, there is shown a block diagram of one of the DC to AC converters 82. As shown, it comprises an inverter circuit 150 and a control circuit 152. The inverter circuit 150 receives DC current on the supply lines 84,86 and supplies an output current to the two lamps 36 of its associated pumping chamber 34. The DC to AC converter 82 is constructed generally in accordance with the principles described in International patent application WO 91/20172.

Figure 11:
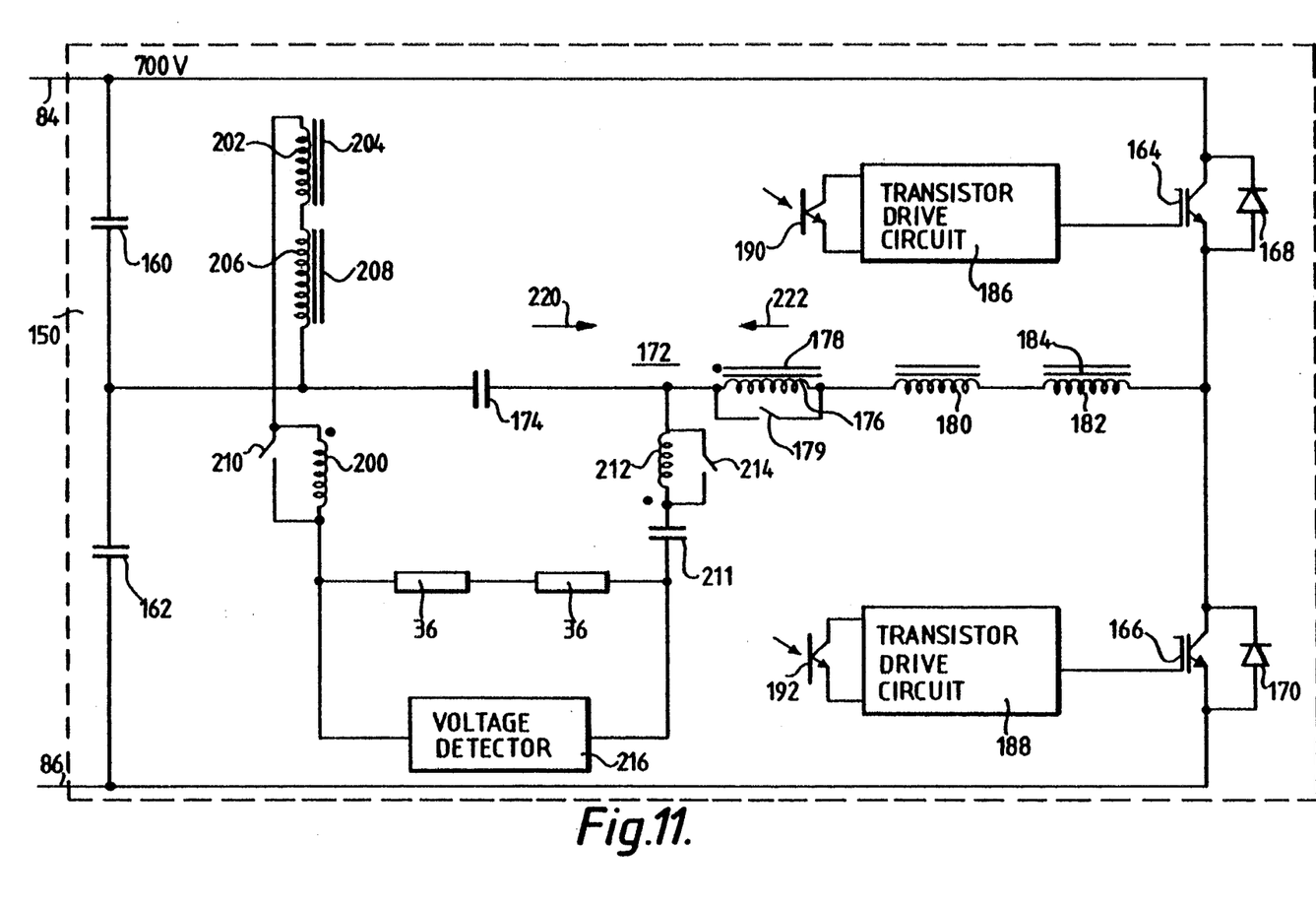
FIG. 11 is a circuit diagram of the inverter circuit forming part of the DC to AC converter of FIG. 10.

Referring now to FIG. 11, there is shown the circuit diagram of the inverter circuit 150. In this circuit, the supply lines 84,86 are connected by a pair of capacitors 160,162 and also by a pair of transistors 164,166. The collectors and emitters of transistors 164,166 are bridged, respectively, by a pair of diodes 168,170. The junction of capacitors 160,162 and the junction of the emitter of transistor 164 and the collector of transistor 166 are connected by a resonant circuit 172. The resonant circuit comprises a capacitor 174, the primary winding 176 of a transformer 178, an inductor 180, and the primary winding 182 of a current sensing transformer 184, connected in series. The primary winding 176 of transformer 178 is bridged by a relay contact 179. The transistors 164,166 are driven, respectively, by a pair of transistor drive circuits 186,188. The drive circuits 186,188 receive input signals, respectively, from a pair of phototransistors 190,192.

The two lamps 36 are connected to form a series circuit. One end of this series circuit is connected to the junction of capacitors 160,174 through a secondary winding 200 of transformer 178, the primary winding 202 of a current sensing transformer 204, and the primary winding 206 of a current sensing transformer 208. The secondary winding 200 is bridged by a relay contact 210. The other end of the series circuit formed by the two lamps 36 is connected through a capacitor 211 and another secondary winding 212 of transformer 178 to the junction of capacitor 174 and transformer 178. The secondary winding 212 is bridged by a relay contact 214. A voltage detector 216 is connected across the series circuit formed by the two lamps 36.

In operation, the transistors 164,166 are switched on alternately so as to cause an alternating current to flow in the resonant circuit 172 at a frequency which corresponds to the natural frequency of the resonant circuit 172. This natural frequency is established primarily by the values of the capacitor 174 and the inductor 180. In the present example, the full load design frequency is set at a value of 25 kHz.

Figure 12:
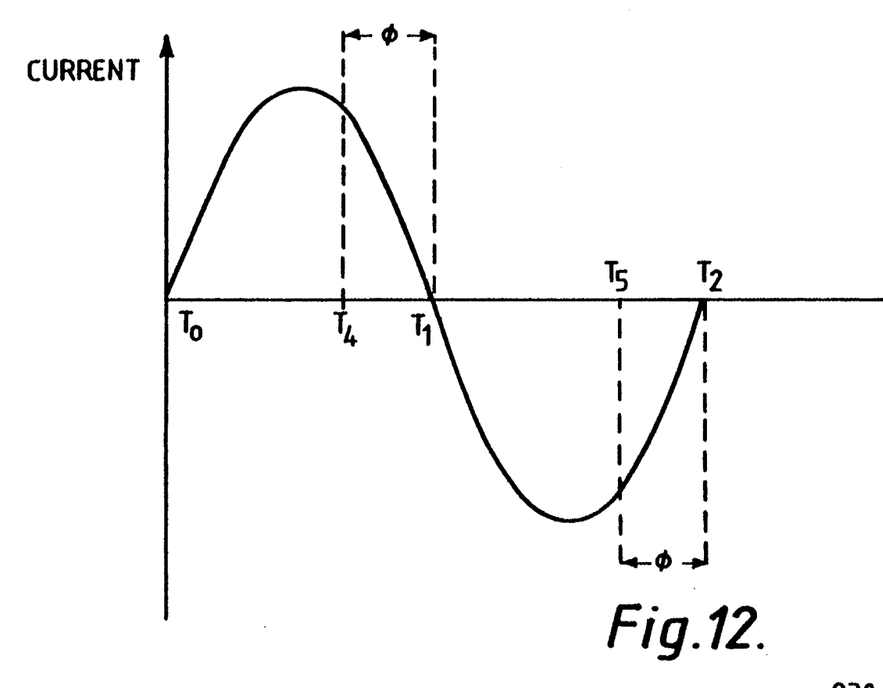
FIG. 12 is a graph illustrating the operation of the inverter circuit of FIG. 11.

The times at which the transistors 164,166 are turned on and off will now be described with reference to FIG. 12, which is a graph of one cycle of the alternating current flowing in resonant circuit 172. The operation will be described initially with the transistors 164,166 switched on and off so as to obtain a maximum value of the current.

At the beginning of the cycle, at a time $T_0$ when the value of the current passes through zero, the transistor 166 is turned on. Consequently, current flows from the supply line 84 through the capacitor 160, through the resonant circuit 172 in the direction of arrow 220, and through the transistor 166 to the negative supply line 86. Then, at a time $T_1$ when the current again passes through zero, the transistor 166 is turned off and the transistor 164 is turned on. Consequently, current flows from the positive supply line 84 through transistor 164, through the resonant circuit 172 in the direction of arrow 222, and through capacitor 162 to the negative supply line 86. At the end of the cycle, at a time $T_2$ when the current again passes through zero, the transistor 164 is turned off and the transistor 166 is turned on and the cycle then repeats. When the inverter circuit is operated in this manner, the voltage across resonant circuit 172 and the current flowing through it are in phase and maximum power is delivered to the lamps 36.

In order to reduce the current flowing through the resonant circuit 172, each of the transistors 164,166 is turned off before the end of the appropriate half cycle. Thus, referring to FIG. 12, in the first half of the cycle, the transistor 166 is turned off at a time $T_4$, which occurs before the time $T_1$ by phase angle $\phi$ equivalent to time interval $(T_1-T_4)$. When transistor 166 is turned off in this manner, current continues to flow through the resonant circuit 172 in the direction of arrow 220 but then flows through diode 168 rather than through transistor 166. In the second half of the cycle, the transistor 164 is turned off at a time $T_5$, which occurs before time $T_2$ by a phase angle $\phi$. When transistor 164 is turned off in this manner, current continues to flow through the resonant circuit 172 in the direction of arrow 222 but outside the resonant circuit 172 the current flows through diode 170 rather than through transistor 164. When the inverter circuit is operated in this manner, there will be a phase difference of $\phi$ between the current flowing through the resonant circuit 172 and the voltage across it. The current and also the power supplied to lamps 36 is also reduced.

More specifically, if the peak current in the lamps 36 has a value $I_{max}$ when each transistor is turned off exactly at the end of the respective half cycle, the peak current flowing through the lamps will be given by $I_{max}.\cos\phi$ when the switch-off times are advanced by a phase angle $\phi$. Thus, the current supplied to lamps 36 may be controlled by controlling the phase angle $\phi$.

It should be noted that the current supplied to lamps 36 is independent of the value of their impedance. By way of modification, the lamps 36 may be connected across the inductor 180 instead of being connected across the capacitor 174.

The inverter circuit includes a circuit for triggering a discharge in the lamps 36 by supplying a relatively high voltage alternating current to them at 25 kHz. In the present example, each lamp is triggered with alternating current having a root mean square voltage of 3 kV.

Figure 13:
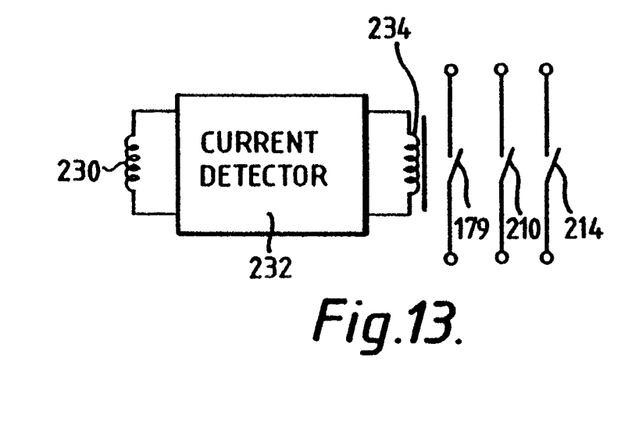
FIGS. 13 and 14 together show the circuit diagram of the control circuit of the DC to AC converter of FIG. 10.

The trigger circuit includes the transformer 178. In order to trigger a discharge in lamps 36, the relay contacts 179,210,214 are open and, consequently, relatively high voltages are produced across the secondary windings 200,212. The current flowing through the lamps 36 is detected by the current sensing transformer 208. As shown in FIG. 13, the secondary winding 230 of this transformer is connected to the input of a current detector 232. When the current through the lamps 36 rises to the intended value, the current detector 232 energises a solenoid coil 234, which in turn closes the relay contacts 179,210,214. The discharge in the lamps 36 is then maintained at a relatively low voltage.

The trigger circuit supplies a repetitive alternating potential to the lamps 36. Ionisation growth under the alternating field leads to a discharge being established at a substantially lower voltage than in the conventional case where a short high voltage pulse is applied. Consequently the design of both the power supply and the pumping sections of the optical head do not have to withstand high voltages and are thus simpler and more reliable than conventional arrangements where high voltage insulation is required.

The current detector 232 forms part of the control circuit 152 for the inverter circuit 150. The remainder of the control circuit 152 will now be described with reference to FIG. 14.

Figure 14:
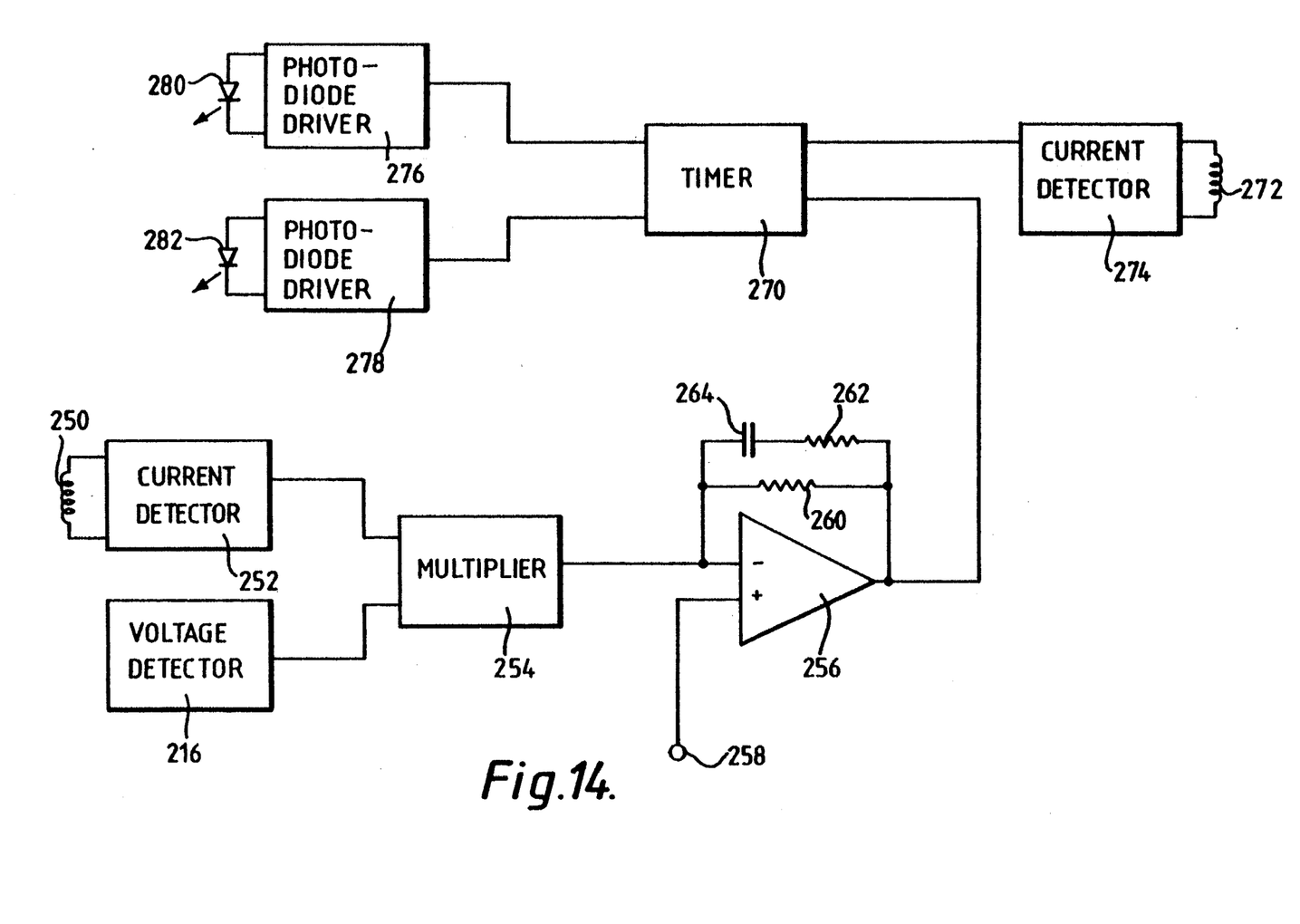

In the control circuit 152, a secondary winding 250 of current sensing transformer 204 is connected to the input of a current detector 252. At its output, the current detector 252 produces a signal which indicates the level of current flowing through lamps 36. This signal is supplied to one input of a multiplier 254, whose other input receives the output signal from the voltage detector 216. Thus, at the output of multiplier 254 there is produced a signal which indicates the combined power output of the two lamps 36.

The output of multiplier 254 is supplied to the inverting input of a differential amplifier 256. The non-inverting input of amplifier 256 receives a power demand signal from the computer 16 via a terminal 258. The output of amplifier 256 is connected to its inverting input through resistors 260,262 and a capacitor 264. Thus, the amplifier 256 is configured as an integrator.

As has been mentioned above, the computer 16 may control the laser system so that it produces either a continuous output beam, having a desired power, or a modulated continuous beam, or a pulsed beam, in which the duration, shape and energy in each pulse as well as the pulse repetition rate have desired values. In order to achieve an output beam having the desired properties, the power demand signal supplied to terminal 258 is set accordingly by computer 16. Thus, the 25 kHz alternating current supplied to the lamps may be regarded as a carrier. This carrier can be supplied to the lamps either unmodified to obtain a continuous output beam, or modulated up to at least 500 Hz to obtain a modulated output beam, or in the form of pulses.

The output of amplifier 256 is connected to one input of a timer 270. The secondary winding 272 of the current sensing transformer 184 is connected to the input of a current detector 274. The output of this current detector indicates the level of current flowing through the resonant circuit 172. The output of current detector 274 is supplied to the other input of timer 270. The timer 270 provides two output signals which are supplied, respectively, to two photodiode drivers 276,278. The photodiode drivers 276,278 energise, respectively, a pair of photodiodes 280,282, which are optically coupled to the opto-transistors 190,192 shown in FIG. 11.

The operation of the control circuit 152 will be described with reference to the graph shown in FIG. 12. At the beginning of a cycle of the alternating current flowing in the resonant circuit 172, that is at time $T_0$, the timer 270 causes the photodiode driver 278 to energise its photodiode 282. This turns on the transistor 166. Then, at time $T_4$, the timer 270 causes the photodiode driver 278 to deenergise its photodiode 282, thereby turning off transistor 166. Thus, the transistor 166 is turned off at a phase angle $\phi$ before the end of the first half of the cycle. The value of the phase $\phi$ is determined by the signal supplied to the timer 270 from the amplifier 256.

In the second half of the cycle, the timer 270 causes the photodiode drive 276 to energise its photodiode 280 at time $T_1$ and thereby turn on transistor 164. At time $T_5$, the timer 270 causes the photodiode driver 276 to deenergise its photodiode 280 and thereby turn off transistor 164.

Consequently, the output power of the lamps 36 corresponds to the power demanded by the computer 16.

Figure 15:
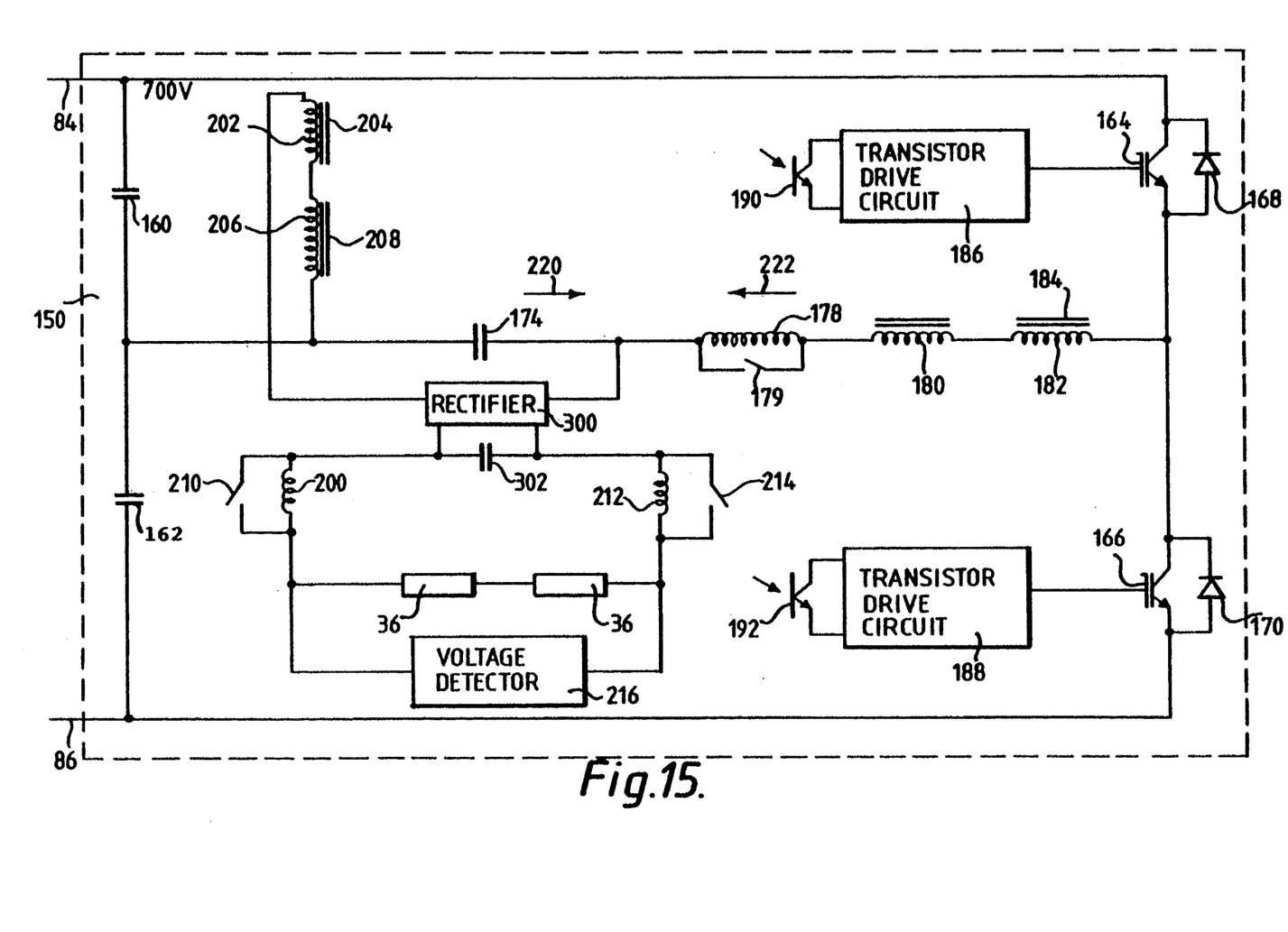
FIG. 15 is a circuit diagram which shows a modification to the inverter circuit of FIG. 11 in which the lamps are provided with rectified alternating current.

Referring now to FIG. 15, there is shown a modification to the inverter circuit 150 in which a full wave rectifier 300 is connected between the capacitor 174 and the lamps 36. Consequently, full wave rectified current is supplied to the lamps 36. In order to complete the circuit for supplying the trigger voltage across lamps 36, a capacitor 302 is connected across the output of rectifier 300. The value of capacitor 302 should be sufficient to permit the trigger current to flow but it should not be so large that it causes significant smoothing in the full wave rectified current. With the modification shown in FIG. 15, the current in the resonant circuit 172 still has a frequency of 25 kHz. However, the full wave rectified current supplied to the lamps 36 has a repetitive waveform having a frequency which is double this value. In comparison with the inverter circuit shown in FIG. 11, the inverter circuit of FIG. 15 has the disadvantage that one of the electrodes in each lamp 36 will wear faster than the other electrode and so the lamps will have a shorter life.

Although in FIGS. 11 and 15 the capacitor 174 is shown as a single capacitor, it is in practice formed from a bank of eight capacitors and it is shown as a single capacitor in order to simplify the drawing. In practice the inductor 180 is a single inductor but, if desired, it may be replaced by two or more inductors to achieve the desired inductance.

We claim:

1. A laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed inside a lamp envelope, and the power supply means being arranged to supply alternating current at a frequency greater than 5 kHz to said at least one lamp, wherein the power supply means comprises a resonant circuit having a pair of reactive elements in the form of an inductor and a capacitor connected in series, said at least one lamp being connected across one of the reactive elements, a first switching device arranged to conduct current from a direct current source in one direction through the resonant circuit, a second switching device arranged to conduct current from the direct current source in the other direction through the resonant circuit, and means for driving the switching devices to conduct alternately and thereby cause an alternating current to flow in the resonant circuit.

2. A laser system as claimed in claim 1, in which the material for supporting a discharge in said at least one lamp comprises a gas.

3. A laser system as claimed in claim 1, in which the power supply means is arranged to supply alternating current at a frequency greater than or equal to 20 kHz.

4. A laser system as claimed in claim 1, in which the power supply means is arranged to supply alternating current at a frequency less than or equal to 100 kHz.

5. A laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed inside a lamp envelope, and the power supply means being arranged to supply rectified alternating current to said at least one lamp, prior to rectification the alternating current having a frequency greater than 5 kHz.

6. A laser system as claimed in claim 5, in which, prior to rectification, the alternating current has a frequency greater than or equal to 20 kHz.

7. A laser system as claimed in claim 6, in which, prior to rectification, the alternating current has a frequency less than or equal to 100 kHz.

8. A laser system as claimed in claim 1, in which the means for driving the switching devices is arranged to vary the phase at which each switching device is turned off relative to the alternating current in accordance with a demand signal.

9. A laser system as claimed in claim 1, in which the direct current source is at least one boost converter.

10. A laser system as claimed in claim 5, in which the pumping section is located in an optical resonator so as to generate an output beam.

11. A laser system as claimed in claim 5, in which there are at least two pumping sections located in the optical resonator.

12. A laser system as claimed in claim 5, including an optical modulator or other switching device located in the optical resonator and arranged to operate in a Q-switched mode.

13. A laser system as claimed in claim 5, including a harmonic generator associated with the optical resonator so as to shorten the wavelength of the output beam.

14. A laser system as claimed in claim 5, including means for monitoring a material processing operation performed by the laser system, and control means responsive to the monitoring means for controlling the power supply means.

15. A laser system comprising a pumping section and means for supplying power to the pumping section, the pumping section comprising a solid or liquid laser medium and at least one lamp for providing pumping energy to the laser medium, said at least one lamp comprising material for supporting a discharge and at least two electrodes sealed in a lamp envelope, and the power supply means comprising at least one boost converter for providing a source of direct current, a resonant circuit having a pair of reactive elements in the form of an inductor and a capacitor connected in series, said at least one lamp being connected across one of the reactive elements, a first switching device arranged to conduct current in one direction from the direct current source through the resonant circuit, a second switching device arranged to conduct current in the other direction from the direct current source through the resonant circuit, and means for driving the switching devices to conduct alternately, and thereby cause an alternating current to flow in the resonant circuit.

16. A laser system as claimed in claim 15, in which the material for supporting a discharge in said at least one lamp comprises a gas.

17. A lasers system as claimed in claim 15, in which the power supply means is arranged to supply alternating current at a frequency greater than or equal to 20 kHz.

18. A laser system as claimed in claim 15, in which the power supply means is arranged to supply alternating current at a frequency less than or equal to 100 kHz.

19. A laser system as claimed in claim 15, in which the pumping section is located in an optical resonator so as to generate an output beam.

20. A laser system as claimed in claim 1, in which the pumping section is located in an optical resonator so as to generate an output beam.

21. A laser system as claimed in claim 15, in which there are at least two pumping sections located in the optical, resonator.

22. A laser system as claimed in claim 1, in which there are at least two pumping sections-located in the optical resonator.

23. A laser system as claimed in claim 15, including an optical modulator or other switching device located in the optical resonator and arranged to operate in a Q-switched mode.

24. A laser system as claimed in claim 1, including an optical modulator or other switching device located in the optical resonator and arranged to operate in a Q-switched mode.

25. A laser system as claimed in claim 15, including a harmonic generator associated with the optical resonator so as to shorten the wavelength of the output beam.

26. A laser system as claimed in claim 1, including a harmonic generator associated with the optical resonator so as to shorten the wavelength of the output beam.

27. A laser system as claimed in claim 15, including means for monitoring a material processing operation performed by the laser system, and control means responsive to the monitoring means for controlling the power supply means.

28. A laser system as claimed in claim 1, including means for monitoring a material processing operation performed by the laser system, and control means responsive to the monitoring means for controlling the power supply means.

* * * * *